United States Patent [19]

Cates et al.

[11] Patent Number: 4,726,822
[45] Date of Patent: Feb. 23, 1988

[54] FAST RESPONSE THERMOCHROMATOGRAPHIC CAPILLARY COLUMNS

[75] Inventors: Marion H. Cates, Largo; William E. Skillman, III, Seminole, both of Fla.

[73] Assignee: Honeywell Inc., Minneapolis, Minn.

[21] Appl. No.: 663,798

[22] Filed: Oct. 22, 1984

[51] Int. Cl.[4] .............................................. B01D 15/08
[52] U.S. Cl. ......................................... 55/267; 55/197;
55/386; 65/3.31; 210/198.2
[58] Field of Search ................. 55/197, 386, 208, 267;
65/3.31; 210/198.2; 219/56, 60 R, 201, 301,
543, 544, 547; 427/51, 52, 92, 98, 123, 126.5,
383.5, 407.2; 428/380, 936

[56] References Cited

U.S. PATENT DOCUMENTS

| | | | |
|---|---|---|---|
| 2,886,470 | 5/1959 | Park et al. | 427/383.5 |
| 2,915,613 | 12/1959 | Norton | 219/543 X |
| 2,977,450 | 3/1961 | Boicey | 219/547 X |
| 3,063,286 | 11/1962 | Nerheim | 55/197 X |
| 3,496,336 | 2/1970 | Hingorany et al. | 219/547 X |
| 3,856,681 | 12/1974 | Huber | 55/386 X |
| 4,156,127 | 5/1979 | Sako et al. | 219/547 X |
| 4,194,536 | 3/1980 | Stine et al. | 219/301 X |
| 4,280,905 | 7/1981 | Gunkel et al. | 210/198.2 |
| 4,293,415 | 10/1981 | Bente, III et al. | 55/386 X |
| 4,321,073 | 3/1982 | Blair | 427/126.2 X |
| 4,418,984 | 12/1983 | Wysocki et al. | 427/383.5 X |

Primary Examiner—Robert Spitzer
Attorney, Agent, or Firm—Mitchell J. Halista; Albin Medved

[57] ABSTRACT

A thermochromatographic column has a fused silica capillary with a high temperature chemically inert polymer coating thereon supporting a thin heater film formed by the deposition of either a high resistance metallic compound auto-catalytically from a solution of the compound or a nichrome film sputtered onto the polymer clad capillary tubing. The electrical contacts to the heater film may be either resistance welded thereto or the electrically conductive wires may be attached to the capillary body and integrated into the heater film during the deposition of the heater film. An outer layer of an electrically insulating material is applied to the heater film to electrically isolate the heater film and to protect the heater film from damage.

13 Claims, 1 Drawing Figure

U.S. Patent  Feb. 23, 1988  4,726,822
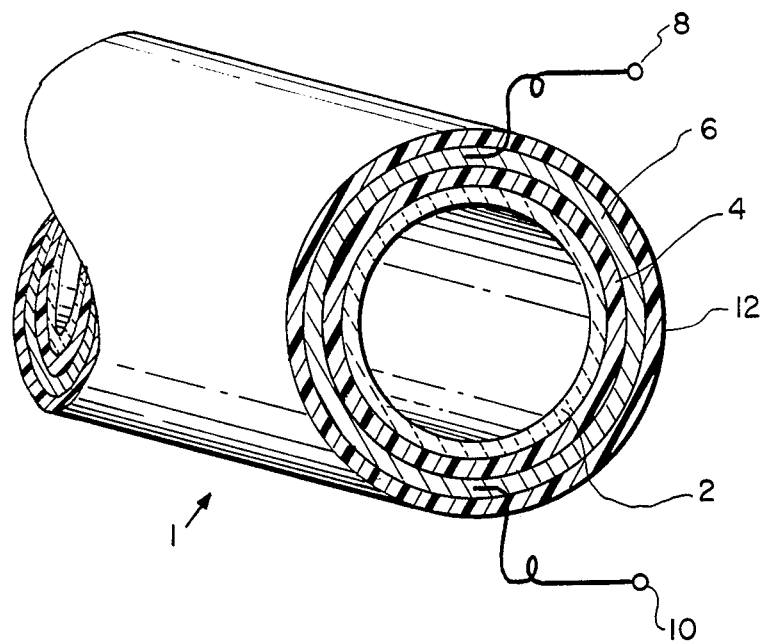

FAST RESPONSE THERMOCHROMATOGRAPHIC CAPILLARY COLUMNS

BACKGROUND OF THE INVENTION

1. Field of the Invention

The present invention is directed to gas analyzers. More specifically, the present invention is directed to a thermochromatographic capillary column for use in a gas chromatography apparatus.

2. Description of the Prior Art

Analytical chemical detectors have been miniaturized into small portable packages to produce field testing devices. In the case of a gas chromatograph, however, further miniaturization has been limited by the need to provide heating means, e.g., an oven, for uniformly and quickly heating a capillary chromatographic column. Such capillary columns do not lend themselves to conventional coil wrapping techniques for superimposing a resistance heater wire on the column, while the use of a space consuming oven is a major factor in preventing the reduction of the gas chromatagraph to a size having a maximized portability, e.g., wrist watch size. The present invention is effective to produce a heated capillary column while avoiding the aforesaid limitations of the prior art to maximize the speed and uniformity of the column's thermal response in a miniature and easily reproducible capillary column structure.

SUMMARY OF THE INVENTION

The object of the present invention is to provide an improved thermochromatographic column.

In accomplishing this and other object, there has been provided, in accordance with the present invention, a chromatographic column having a capillary means having an outer surface and a heater layer deposited on the outer surface of the capillary.

BRIEF DESCRIPTION OF THE DRAWING

A better understanding of the present invention may be had when the following detailed description is read in connection with the accompanying drawing, in which the single FIGURE is a cross-sectional illustration of a chromatographic column embodying an example of the present invention.

DESCRIPTION OF THE PREFERRED EMBODIMENT

Detailed Description

Referring to the single FIGURE drawing in more detail, there is shown a chromatographic column 1 having a fused silica capillary 2. The outer surface of the capillary 2 is coated with a layer 4 of a chemically inert, high temperature polymer material, e.g., a polymide resin. The outer surface of the polymer layer is uniformly coated with a thin heater film 6 having electrically terminals 8 and 10 attached thereto, e.g., at respective ends of the film 6. The terminals 8,10 would prefereably be in the form of electrically conductive rings encircling and in contact with respective ends of the heater film 6 to produce a uniform current flow through the heater film 6. The outer surface of the heater film 6 is, in turn, coated with a layer 12 of a high temperature, chemically inert polymer which may be the same material used for the inner polymer coating 4.

The uniform depositing of the heater directly on the surface of the capillary column 1 provides several advantages by eliminating coil wrapping of a resistance heater wire on the column, providing uniformity of a thermal energy along the length of the column and a fast thermal response by direct contact of the deposited heater film with the capillary 2. Fused silica capillary columns are available in several sizes, e.g., 0.3 mm O.D. and are very flexible to allow bending and coiling to a desired configuration. Accordingly, the wrapping of a heater wire on such a column would be extremely difficult, if not virtually impossible.

The present invention is effective to overcome all of the aforesaid problems by providing a heated capillary column having a heater material deposited as a thin film directly on the polymer clad capillary column. Two methods are proposed for achieving such a heater clad column structure. The first method involves the deposition of a heater film by an auto-catalytic process from a solution of a metallic compound having a suitable electrical resistance, e.g., nickel phosphide. This material possesses a specific resistivity of $75 \times 10^{-8}$ ohm meters or about three quarters that of nichrome. By employing known wire plating equipment such as that used to plate magnetic wire memories, the electroless nickel deposit may be quickly and uniformly deposited on the polymer clad column 1. The advantages of employing electroless nickel phosphide, in addition to its desirable specific resistivity, are that it forms a passive surface which is not prone to oxidation and its coefficient of thermal expansion matches that of fused, or glassy, silica to provide a good thermal match thereto to avoid thermal stresses. A sequence for producing the deposit may include an initial light vapor hone or abrasion of the polyimide surface using a microbead and water slurry. This is followed by a distilled water rinse and a catalyzing with a 0.04% solution of palladium chloride followed by a dip in a 5% stannous chloride solution. A subsequent distilled water rinse is followed by a removal of any residual stannous chloride by a dip into a 5% solution of perchloric acid. A subsequent final water rinse is followed by the nickel phosphide electroplating.

An alternate or second method employs a known cathodic sputtering technique for depositing a nichrome film having a specific resistivity of 100 to $112 \times 10^{-8}$ ohm meters. This nichrome film can be sputtered directly over the polyimide clad capillary tubing. By controlling the cathode current and optimizing the radio frequency input in the inert gas environment of the sputtering chamber, a uniform nichrome deposit can be realized and the thickness of the nichrome film can be controlled. The sputtering is performed at a typical sputtering chamber pressure of $10^{-1}$ to $10^{-2}$ Torr and involves an inert gas environment using a fill gas such as argon or helium.

Electrical contacts 8, 10 for connecting the heater element 6 to a power supply may be provided by either resistance welding electrical terminals to the heater film or tying terminal wires to the respective ends of the capillary body on the polymer layer 4 and integrating the ends of the terminal wires into the heater film 6 during the deposition process. An outer polydimide sheath or cover 12 may be applied to the outside surface of the heater film 6 to prevent damage to the heater film 6 and to provide electrical isolation thereof. The inner surface of the capillary 2 would be subsequently coated with a suitable adsorbant material to enable the capillary to function as a chromatographic column by selectively retarding constituents of a sample to be analyzed flowing through the column.

Accordingly, there may been seen that there has been provided, an improved chromatographic column.

The embodiments of the present invention in which an exclusive property or privilege is claimed are defined as follows:

1. A chromatographic column comprising capillary means having an outer surface and heater means including a resistive material in the form of a uniform homogeneous film deposited as a continuous enveloping layer completely covering said outer surface of said capillary means wherein said resistive film includes a sputtered film of nichrome deposited on said surface of said capillary means.

2. A chromatographic column as set forth in claim 1 wherein said resistive film includes electrical terminal means connected to respective ends of said resistive film.

3. A chromatographic column as set forth in claim 2 wherein said terminal means include electrically conductive bands encircling and in contact with said respective ends of said resistive film.

4. A chromatographic column as set forth in claim 1 wherein said capillary means includes a fused silica tube having an outer layer of a high temperature chemically inert polymer forming said outer surface.

5. A chromatographic column as set forth in claim 4 wherein said heater means includes an outer layer of a high temperature, chemically inert polymer on said resistive film.

6. A chromatographic column comprising capillary means having an outer surface and heater means including a resistive material in the form of a uniform homogeneous film deposited as a continuous enveloping layer completely covering said outer surface of said capillary means wherein said resistive film includes a nickel phosphide layer deposited on said outside surface of said capillary.

7. A chromatographic column as set in claim 6 wherein said resistive film includes electrical terminal means connected to respective ends of said heater means.

8. A chromatographic column as set forth in claim 7 wherein said terminal means include electrically conductive bands encircling and in contact with respective ends of said resistive film.

9. A chromatographic column as set forth in claim 6 wherein said capillary means includes a fused silica tube having an outer layer of a high temperature, chemically inert polymer forming said outer surface.

10. A chromatographic column comprising capillary means having an outer surface and heater means including a resistive material in the form of a uniform homogeneous film deposited as a continuous enveloping layer completely covering said outer surface of said capillary means wherein said capillary means includes a fused silica tube having an outer layer of a high temperature chemically inert polymer forming said surface and wherein said heater means includes an outer layer of a high temperature, chemically inert polymer on said resistive film and wherein said resistive film includes a nickel phosphide layer deposited on said outer layer on said capillary means.

11. A chromatographic column as set forth in claim 10 wherein said heater means includes electrical terminal means connected to respective ends of said resistive film.

12. A chromatographic column comprising capillary means having an outer surface and heater means including a resistive material in the form of a uniform homogeneous film deposited as a continuous enveloping layer completely covering said outer surface of said capillary means wherein said capillary means includes a fused silica tube having an outer layer of a high temperature chemically inert polymer forming said outer surface and wherein said heater means includes an outer layer of a high temperature, chemically inert polymer on said resistive film and wherein said resistive film includes a sputtered film of nichrome deposited on said outer layer on said capillary means.

13. A chromatographic column as set forth in claim 12 wherein said resistive film includes electrical terminal means connected to respective ends of said heater means.

* * * * *